United States Patent [19]

Kirchubel

[11] 4,056,609
[45] Nov. 1, 1977

[54] ARTICLE FOR DIAGNOSIS OF ACHLORHYDRIA

[75] Inventor: Michael A. Kirchubel, San Francisco, Calif.

[73] Assignee: Gunn, Kirchubel & Miller, San Francisco, Calif.

[21] Appl. No.: 653,000

[22] Filed: Jan. 28, 1976

[51] Int. Cl.$^2$ ............... A61K 43/00; A61K 29/00; G01N 31/00; G01N 33/00
[52] U.S. Cl. ................. 424/1; 195/103.5 R; 252/408; 424/9
[58] Field of Search ......... 424/1, 1.5, 7, 9, 4, 424/32, 35, 94; 23/230 B, 253 TP; 252/408; 195/103.5 R

[56] References Cited

U.S. PATENT DOCUMENTS

| 2,791,533 | 5/1957 | Segal et al. | 424/9 |
| 2,992,166 | 7/1961 | Sigg et al. | 424/7 |
| 3,444,290 | 5/1969 | Wai | 424/4 |
| 3,538,214 | 11/1970 | Polli et al. | 424/32 |
| 3,904,373 | 9/1975 | Harper | 424/7 X |

FOREIGN PATENT DOCUMENTS

| 57.25M | 1/1968 | France | 424/7 |
| 2,035,739 | 1/1972 | Germany | 424/32 |
| 7,108,719 | 8/1969 | Japan | 424/35 |
| 779,303 | 7/1957 | United Kingdom | 424/9 |
| 850,426 | 10/1960 | United Kingdom | 424/9 |

*Primary Examiner*—Benjamin R. Padgett
*Assistant Examiner*—Christine M. Nucker
*Attorney, Agent, or Firm*—Warren, Chickering & Grunewald

[57] ABSTRACT

There is disclosed an article for diagnosis of achlorhydria which includes an agent which is readily detectable when released in the stomach, the agent being enclosed in a fluid-impervious entrapping medium which is degraded in acidic fluids to release the agent.

22 Claims, No Drawings

ARTICLE FOR DIAGNOSIS OF ACHLORHYDRIA

BACKGROUND OF THE INVENTION

Achlorhydria is a condition characterized by stomach fluids that are not acidic. Achlorhydria may be a disorder in itself which characteristically produces symptoms of digestive problems. Frequently achlorhydria is a symptom of a different disorder such as cancer of the stomach or certain nervous disorders.

Achlorhydria is difficult to detect without an uncomfortable and professionally administered procedure. The procedure for detecting achlorhydria usually involves introduction of analysis or sampling devices into the patient's stomach to provide either a direct reading of stomach fluid pH or a sample for analysis. In either case, a tube must be inserted down the patient's throat which produces the usual problems of patient resistance and gagging, and as a result tests for achlorhydria are adminstered far less frequently than they should be.

A simple, reliable, and comfortably administered test for achlorhydria is needed. If such a test were available, it could be given routinely as part of regular medical checkups to provide an early warning for serious stomach problems and a reliable indication of the acidity of a patient's stomach fluid.

THE INVENTION

This invention is an inexpensive, reliable, easily administered article that is useful to detect the presence of stomach acid. The article includes a detection agent that is entrapped in a fluid-impervious entrapping medium. The entrapping medium includes material that is degradable at pH lower than 6 which, when degraded, permits the release of the entrapped detection agent from the entrapping medium.

A detection agent is normally a material which exerts little or no physiological effect on the individual but its presence, when released from its entrapment, is easily determined. A typical detection agent is methylene blue, which when released in the stomach, imparts a characteristic color to the urine. Other substances which color the urine include phenol red and Pyridium (phenazopyridine HCl). Detection agents which cause the patient's urine to fluoresce such as sodium fluorescein, riboflavin, or quinine may be used. A detection agent may be a substance not normally found in the urine or blood such as sodium bromide, potassium iodide, or phenolphthalein. A detection agent such as methyl mercaptan may cause the urine or stool to have an unusual odor. A detection agent may color the stool. Examples of this type include unabsorbable dyes, charcoal, bismuth subnitrate, manganese dioxide, or reduced iron. The drug Flagyl (metronidazole) may cause the patient to experience an unusual taste. Potassium iodide, when released in the stomach, is detectable in the saliva. Sodium fluorescein will cause discoloration of the skin or sclera. The detection agent may be one whose presence in the body in either compact (entrapped) or diffuse (released) form may be determined by mechanical means. Such detection agents may be radioactive or radio-paque materials. Finally, the detection agent may be a substance which produces an easily observable physiological effect such as a flatulent, diuretic, myotic, or midriatic.

The entrapping medium is one which is impervious to stomach fluids. The entrapping medium includes a degradable element which is degradable when subjected to stomach fluids at normal low pH. The entire entrapping medium or only a portion of it may be degradable when that portion is adapted to release the entrapped agent when it is degraded.

The entrapping medium may be degraded by any degree of acidity, or it may be degraded only in specific pH ranges. By suitable selection of degradable materials, a quantitative measure of a patient's stomach acidity may be obtained.

One suitable entrapping medium useful in this invention is based on magnesium, either as the entrapping medium, per se, or as an integral part of the entrapping medium which degrades in normal stomach acid to release the detection agent entrapped in a fluid-impervious material. As an example, an enclosure of rubber of suitable physiologically inert plastic may be sealed with a thin magnesium ribbon. At pH lower than 2.3, the magnesium readily degrades to break the seal and release the detection agent maintained within the rubber or plastic enclosure. Since normal stomach fluid is usually at a pH lower than 2.3, the magnesium based article of the present invention may readily detect normal stomach acidity for most patients simply by ingesting it and monitoring the patient for the presence of the detection agent, for example, his urine, for a period of approximately twelve hours. If the patient has normal stomach acid, the ingested articles of this invention will degrade in the patient's stomach releasing the detection agent, for example, methylene blue, which will color the patient's urine a characteristic green color within hours after ingestion.

If a patient suffering from achlorhydria ingests such an article of this invention, the high pH in the person's stomach — normally above 6 — will not degrade the entrapping medium so that the detection agent, for example, methylene blue, will pass through the patient's entire digestion system within the entrapping medium, and the absence of colored urine will indicate that the patient is suffering from achlorhydria. When stomach acid alone is the degrading medium, it is referred to herein as an intrinsic degrading medium.

Another entrapping medium may include the combination of cellulose and the enzyme cellulase which causes cellulose to degrade. Such an entrapping medium requires a pH between 3 and 6 to be degraded because cellulase is not active to degrade cellulose at pH lower than 3 or higher than 6. A cellulose-cellulase based entrapping medium could be ingested with a quantity of antacid or buffering material so that any stomach acidity which would cause the patient's stomach fluids to be at pH lower than 6 would either be in the range at which cellulase would degrade cellulose at the time the article is ingested, or it would pass through that range due to the action of the antacid in raising the pH of the stomach fluids. When a degrading medium is ingested with the article of this invention rather than being already present in the stomach, such a degrading medium is referred to herein as an extrinsic degrading medium.

DETAILED DESCRIPTION OF THE INVENTION

The invention may be better explained with reference to the following examples which illustrate specific embodiments of the invention and are intended to be illustrative rather than limiting on its scope.

EXAMPLE 1

An article embodying this invention was prepared by filling a short length of rubber tubing with methylene blue crystals. The tubing was selected to be one that is not permeable to the fluids found in a human digestive tract. After being filled with methylene blue crystals, the tubing was rolled tightly and sealed by twisting a piece of thin magnesium ribbon around the rolled tubing to prevent it from becoming unrolled. The magnesium ribbon was 0.006 inches thick, 0.0125 inches wide and long enough to perform its function of sealing the rolled rubber tubing.

A 100 ml quantity of 0.1 normal hydrochloric acid was placed in a beaker as a simulated stomach fluid. The rubber tubing sealed with magnesium was placed in the beaker. The methylene blue crystals were shielded from the hydrochloric acid solution as was evidenced by the fact that the hydrochloric acid remained a water white solution. In about 140 minutes, the magnesium tubing degraded, the rubber tube unrolled, and methylene blue was released into the acid solution as could be observed by the appearance of a dark stain in the solution.

EXAMPLE 2

A number of detection devices embodying this invention were prepared in accordance with Example 1. Several beakers were prepared to contain 100 ml quantities of 0.1 normal hydrochloric aicd which had been titrated with sodium hydroxide so that each beaker contained fluid at a different pH. The pH in the respective beakers was 1, 2, 3, 4, 5, 6 and 7. One detection device was placed in each beaker. After a period of three hours, the detection devices in beakers containing fluid of pH 1 and pH 2 had opened and the fluid was darkly stained by the methylene blue. After a period of 24 hours, the devices which were placed in beakers having pH 3 and above had not opened.

EXAMPLE 3

The device embodying this invention was prepared in the form of a thin-walled rubber tubing containing methylene blue crystals which was tightly rolled and bound with a strip of cellulose in the form of filter paper. A 200 mg quantity of cellulase was maintained outside of the entrapping medium but as a portion of the device. The cellulase was Meicelase-P enzyme, a trade name of Meiji Seika Kaisha Company of Tokyo, Japan, which is employed to identify a cellulase enzyme prepared from trichodermi viride fungi. A solution of 0.1 normal hydrochloric acid was titrated to pH of 6.5 with sodium hydroxide. Into a 20 ml quantity of this solution, the device described hereinabove was placed, and the solution was maintained at 37° C with slight agitation for a period of eight hours. After the eight hour period, the device remained unopened, and the dye was not released from within the rubber tubing.

EXAMPLE 4

A device made in accordance with Example 3 was placed in 20 ml of a solution of 0.1 normal hydrochloric acid titrated to a pH of 2.5 with sodium hydroxide. The solution was maintained at a temperature of 37° C, and it was slightly agitated. After one-half hour in the solution, the device remained unopened, and the pH of the solution was adjusted with sodium hydroxide to 3.5. Agitation was continued for another half hour, and the packet still remained unopened. The pH was again adjusted with sodium hydroxide to 4.5. Each half hour the pH of the solution was raised 1 pH increment. Before the pH of the solution reached 6, the packet had opened, and the entrapped dye had been released.

It is evident from the foregoing description and examples that the present invention concerns any entrapping medium which includes a degradable element that is sensitive to acid and which contains a detection agent. Devices wherein the entrapping medium itself is degradable in an acidic environment are within the scope of this invention. The invention also includes devices containing a number of different detection agents that are released at different pH levels so that a diagnosis may be made not only of achlorhydria but also of a degree of hypochlorhydria, for example, for a patient suffering from insufficient stomach acids rather than a complete absence of stomach acid.

This device may be used alone or in conjunction with drugs which stimulate the secretion of hydrochloric acid such as histamine phosphate, caffeine, or betazole hydrochloride.

What is claimed is:

1. An article useful to detect stomach acid comprising a detection agent enclosed in a fluid-impervious entrapping medium with said entrapping medium including a degradable element that is degradable at pH lower than 6, with said degradable element sealing said entrapping medium whereby when said degradable element is degraded, said detection agent is released from said entrapping medium.

2. The article of claim 1 wherein said degradable element is degraded at pH lower than 2.3.

3. The article of claim 2 wherein said degradable element is magnesium.

4. The article of claim 1 wherein said degradable element is degraded between pH 3 and pH 6.

5. The article of claim 4 wherein said degradable element is a cellulase-degradable form of cellulose and cellulase.

6. The article of claim 1 wherein said detection agent is a dye that colors urine.

7. The article of claim 6 wherein said detection agent is methylene blue.

8. The article of claim 6 wherein said detection agent is phenol red.

9. The article of claim 6 wherein said detection agent is phenazopyridine hydrochloride.

10. The article of claim 1 wherein said detection agent causes urine to fluoresce.

11. The article of claim 10 wherein said detection agent is sodium fluorescein.

12. The article of claim 10 wherein said detection agent is riboflavin.

13. The article of claim 10 wherein said detection agent is quinine.

14. The article of claim 1 wherein said detection agent is chemically detectable in urine.

15. The article of claim 14 wherein said detection agent is phenolphthalein.

16. The article of claim 1 wherein said detection agent is detectable in saliva.

17. The article of claim 16 wherein the detection agent is potassium iodide.

18. The article of claim 1 wherein the detection agent is a substance which produces a physiological effect.

19. The article of claim 18 wherein the detection agent is a myotic.

20. The article of claim 18 wherein the detection agent is a midriatic.

21. The article of claim 1 wherein said detection agent is a radioactive material.

22. The article of claim 1 including a multiple of entrapping mediums, said entrapping mediums containing different detection agents and being sealed by degradable elements that are degraded at different pH levels.

* * * * *